(12) United States Patent
Suryanarayanan et al.

(10) Patent No.: US 8,014,578 B2
(45) Date of Patent: Sep. 6, 2011

(54) METHOD AND SYSTEM FOR IMAGE SEGMENTATION USING MODELS

(75) Inventors: Srikanth Suryanarayanan, Bangalore (IN); Rakesh Mullick, Bangalore (IN); Mitali Janardan More, Mumbai (IN); Krishna Seetharam Shriram, Bangalore (IN)

(73) Assignee: General Electric Company, Niskayuna, NY (US)

( * ) Notice: Subject to any disclaimer, the term of this patent is extended or adjusted under 35 U.S.C. 154(b) by 1087 days.

(21) Appl. No.: 11/702,370

(22) Filed: Feb. 5, 2007

(65) Prior Publication Data
US 2008/0188734 A1   Aug. 7, 2008

(51) Int. Cl.
G06K 9/00   (2006.01)

(52) U.S. Cl. ......... 382/128; 382/131; 382/294; 382/298

(58) Field of Classification Search ............... 382/128, 382/131, 294, 298
See application file for complete search history.

(56) References Cited

U.S. PATENT DOCUMENTS

| | | | |
|---|---|---|---|
| 5,014,334 A | 5/1991 | Fukuhara et al. | |
| 6,144,772 A | 11/2000 | Garland et al. | |
| 6,633,674 B1 | 10/2003 | Gemperline et al. | |
| 6,891,973 B1 | 5/2005 | Atsumi et al. | |
| 6,912,319 B1 | 6/2005 | Barnes et al. | |
| 7,123,760 B2 | 10/2006 | Mullick et al. | |
| 7,177,453 B2 | 2/2007 | Suryanarayanan et al. | |
| 7,181,381 B1 | 2/2007 | Akkaram et al. | |
| 7,254,273 B2 | 8/2007 | Sakanashi et al. | |
| 7,310,435 B2 | 12/2007 | Mallya et al. | |
| 7,471,086 B2 | 12/2008 | Mullick et al. | |
| 7,676,257 B2 | 3/2010 | Suryanarayanan et al. | |
| 2004/0139121 A1 | 7/2004 | Nagaraj et al. | |
| 2006/0176306 A1 | 8/2006 | Nagaraj et al. | |
| 2006/0239553 A1* | 10/2006 | Florin et al. | 382/173 |
| 2008/0095465 A1 | 4/2008 | Mullick et al. | |
| 2008/0101676 A1* | 5/2008 | Zheng et al. | 382/131 |
| 2008/0188741 A1 | 8/2008 | Mallya et al. | |
| 2008/0188962 A1 | 8/2008 | Suryanarayanan et al. | |
| 2008/0232700 A1 | 9/2008 | Gering et al. | |
| 2009/0010540 A1 | 1/2009 | Mullick et al. | |
| 2009/0161939 A1 | 6/2009 | Wu et al. | |

OTHER PUBLICATIONS

Wierzbicki et al "Mapping Template Heart Models to Patient Data Using Image Registration", C. Barillot, D.R. Haynor, and P. Hellier (Eds.): MICCAI 2004, LNCS 3216, pp. 671-678, 2004).*

Marie-Pierre Jolly "Automatic Segmentation of the Left Ventricle in Cardiac MR and CT images" International Journal of Computer Vision 70(2), 151-163, 2006; 2006 Springer Science + Business Media, LLC. Manufactured in The Netherlands. DOI: 10.1007/s11263-006-7936-3.*

(Continued)

*Primary Examiner* — Tom Y Lu
(74) *Attorney, Agent, or Firm* — Scott J. Asmus

(57) ABSTRACT

A technique is provided for utilizing a model of an anatomical feature to facilitate the segmentation of the anatomical feature from its background in a medical image. A global alignment of the model with a region in the patient's image data that generally corresponds to the anatomical feature is performed in one embodiment. Internal structural features within the model are then aligned with their corresponding structural features in the patient's image data. The portion of the patient's image data that is aligned with the model of the anatomical feature is then segmented from the remaining portions of the patient's image data that are not aligned with the model.

15 Claims, 7 Drawing Sheets

OTHER PUBLICATIONS

Chen et al "3D Cardiac Anatomy Reconstruction Using High Resolution CT Data" C. Barillot, D.R. Haynor, and P. Hellier (Eds.): MICCAI 2004, LNCS 3216, pp. 411-418, 2004. Springer-Verlag Berlin Heidelberg 2004.*

Park, et al.; "Region-of-Interest Coding Based on Set Partitioning in Hierarchical Trees", IEEE Transactions on Circuits and Systems for Video Technology, vol. 12, No. 2, Feb. 2002, pp. 106-11.

Krishnan, Karthik; "Efficient Transmission of Compressed Data for Remote Volume Visualization"; IEEE Transactions on Medical Imaging, vol. 25, No. 9, pp. 1189-1199, Sep. 2006.

Lawler, PL; "Coronary CT Angiography", Online Supplement to Applied Radiology, Jul. 30-36, 2004.

Metaxas, D., et al.; Cardiac Segmentation from MRI-Tagged and CT Images, in Proc. 8th WSEAS International Conf. on Computers, 2004.

Frangi, A.F., et al.; "Three-dimensional cardiovascular image analysis", IEEE Trans Medical Imaging, vol. 21, No. 9, Sep. 2002.

Park, H., et al.; "Construction of an Abdominal Probabilistic Atlas and its Application in Segmentation", IEEE Trans Medical Imaging, vol. 22, No. 4, Apr. 2003.

Rohlfing, T., et al.; "Evaluation of atlas selection strategies for atlas-based image segmentation with application to confocal microscopy images of bee brains", NeuroImage, 21, 1428-42, 2004.

Nissen, W., et al.; "Model Based Segmentation of Cardiac and Vascular Images", IEEE Trans on Medical Imaging, 20 (1):2-25, 2001.

Makela, T., et al.; "A Review of cardiac image registration methods", IEEE Transactions on Medical Imaging, vol. 21, No. 9, Sep. 2002.

Haage, P., et al.; "Reduction of contrast material dose and artifacts by a saline flush using a double power injector in helical CT of the thorax", AJR 174 (2000).

Hooper, K.D., et al.; "Thoracic spiral CT: delivery of contrast material pushed with injectable saline solution in a power injector", Radiology 205 (1997), 269-271 (Abstract only).

Bae, K.T., et al.; "Aortic and hepatic peak enhancement at CT: effect of contrast medium injection rate—pharmacokinetic analysis and experimental procine model", Radiology 206 (1998), 455-464 (Abstract only).

Rohlfing, T., et al.; "Bee Brains, B-Splines and Computational Democracy: Generating an Average Shape Atlas", IEEE Workshop on Mathematical Methods in Biomedical Image Analysis, IEEE Computer Society, Los Alamitos, CA, (2001), Kauai, 187-194.

Bae, K.T., et al.; "Peak contrast enhancement in CTA and MRA: When does it occur and why?" Radiology 227 (2003, 809-816.

Lorenzen, P., et al.; "Unbiased Atlas Formation via Large Deformations Metric Mapping", Proc. MICCAI, Oct. 2005, 411-418.

Park, H., et al.; "Least Biased Target Selection in Probabilistic Atlas Construction", Proc. Miccai, 2005, 419-426.

* cited by examiner

METHOD AND SYSTEM FOR IMAGE SEGMENTATION USING MODELS

BACKGROUND

The invention relates generally to medical imaging, and more particularly to a technique for image segmentation using a model.

Medical imaging has become an extremely valuable tool in the diagnosis ad treatment of many illnesses and diseases. For example, cardiac imaging using computed tomography (CT) is emerging as the protocol of choice for the diagnosis and treatment of cardiovascular disease. In addition to standard X-ray systems that produce an image on a film, medical imaging systems are now available that produce digital images that may be displayed on a monitor.

Digital imaging processing enables medical images to be enhanced through the use of computers. Digital image processing has many of the same advantages in signal processing over analog image processing as does digital audio processing over analog audio processing. In addition, digital image processing enables the use of algorithms to perform other tasks, such as three-dimensional visualization and image segmentation.

In digital image processing, segmentation is the partitioning of a digital image into multiple regions in accordance with a given set of criteria. Typically, the goal of segmentation is to locate objects of interest, such as the heart, and separate them from objects of lesser or no interest. For example, segmentation of the heart and its internal structures, such as the four chambers of the heart, is a pre-requisite for three-dimensional visualization of the heart and for performing a quantitative analysis of the function of the heart. This can be very valuable information for the diagnosis and treatment of cardiovascular disease. However, heart segmentation is challenging due a number of factors. One factor is the natural variability in the intensity of the image of the chambers of the heart, which is enhanced by the addition of a contrast agent. Contrast agents are used to selectively highlight anatomical structures, such as blood vessels, and organs, such as the heart and liver. Variations in the injection mechanism may cause these structures to vary in intensity from image to image. In addition, the unpredictability of patient metabolism and the use of new acquisition protocols, such as the saline flush protocol, further complicate the task, making intensity based segmentation tools unreliable.

A need exists for a technique for performing image segmentation that overcomes the problems and difficulties in current imaging systems. In particular, there is a need for an image segmentation technique that does not rely on image intensity consistency across an anatomical feature. The technique provided below may solve one or more of the problems described above.

BRIEF DESCRIPTION

The present technique provides a novel approach for automatically segmenting an anatomical feature from its background by using a model of the anatomical feature. The model of an anatomical feature is used to identify the portion of an image of a patient's internal anatomy to be segmented. A global alignment is performed of the model with a region in the patient's image data that generally corresponds to the anatomical feature. As part of the global alignment, the model may be re-sized to conform with the region in the patient's image data that generally corresponds to the anatomical feature. Internal structural features within the model may then be aligned with their corresponding structural features in the patient's image data. The shape of the internal structural features of the model may be deformed to bring the model into alignment with the anatomical feature in the patient's image data. The portion of the patient's image data that is aligned with the model of the anatomical feature may then be segmented from the remaining portions of the patient's image data that are not aligned with the model.

A model of an anatomical feature may be established in a number of different ways. The model may be based on one or more segmented images of the anatomical feature. For example, the model of the anatomical feature may be an average of a plurality of different segmented images. Alternatively, a method may be used to establish the single segmented image that best represents the average of all of the segmented images. In addition, the model may be established based on the patient's demographics. For example, the model may be established from one or more segmented images with the same gender, age, height, weight, ethnicity, etc., as the patient.

DRAWINGS

These and other features, aspects, and advantages of the present invention will become better understood when the following detailed description is read with reference to the accompanying drawings in which like characters represent like parts throughout the drawings, wherein.

Figure 8:
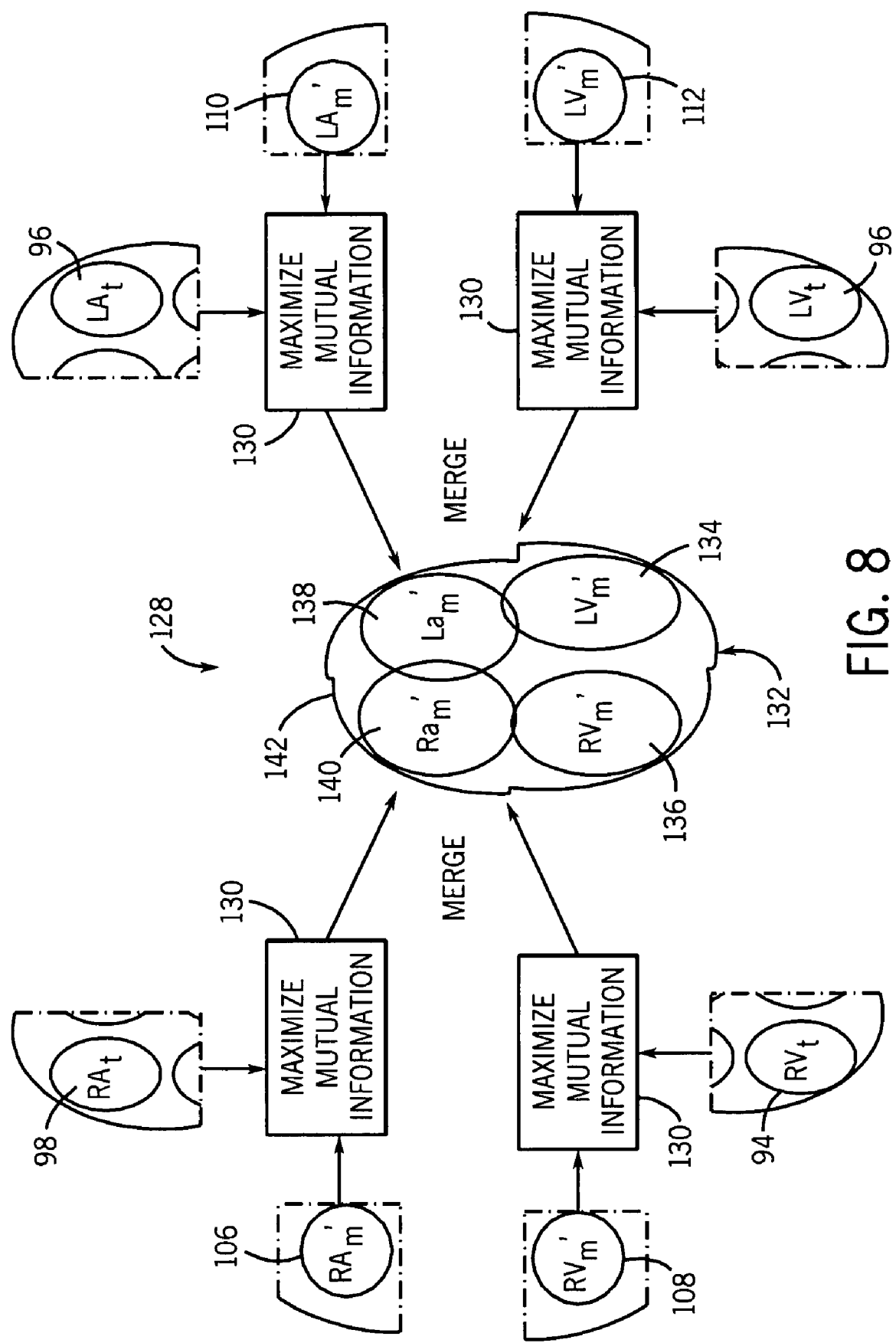
Figure 9:
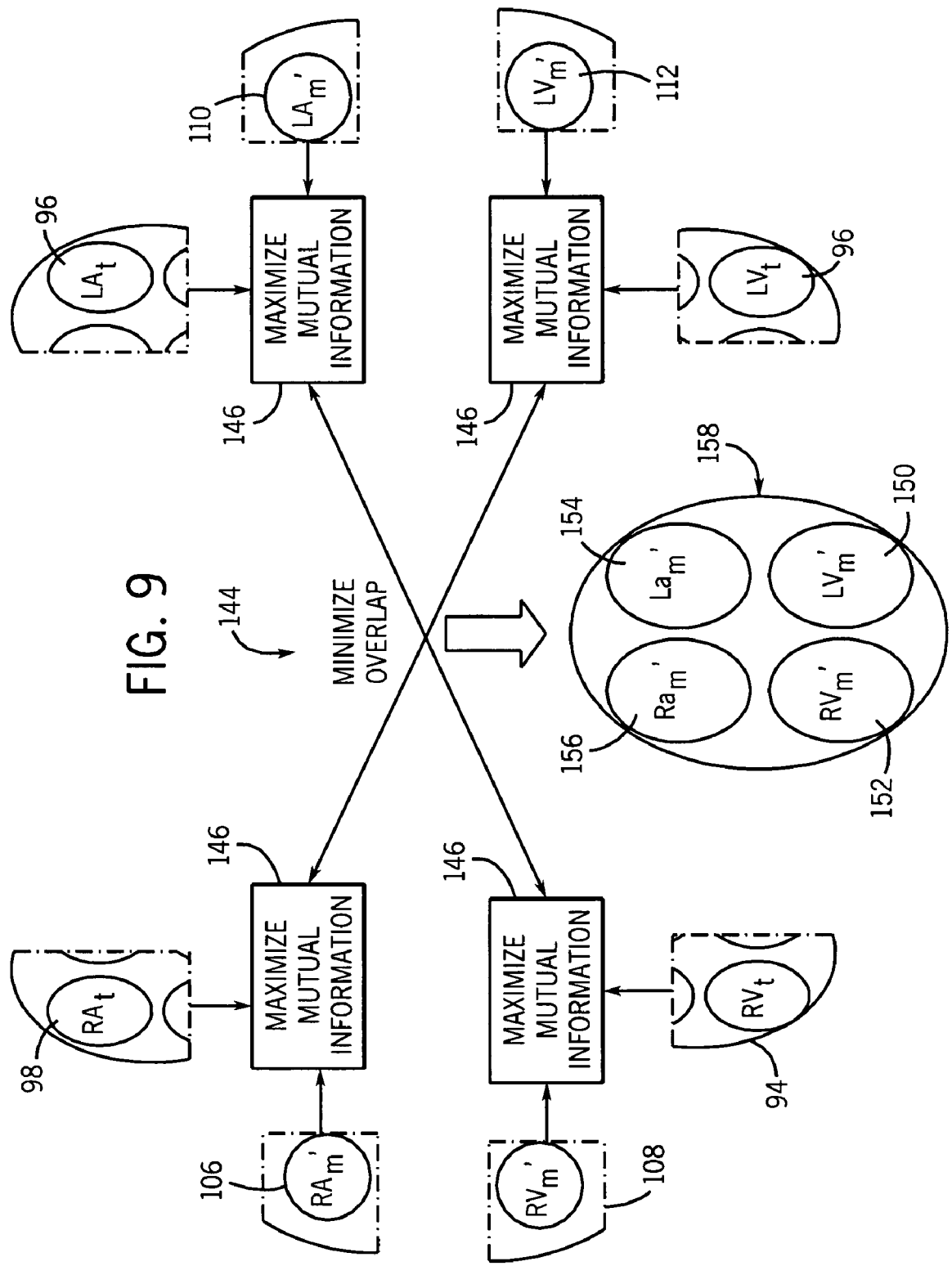

FIG. 8 is a schematic representation of another technique for locally aligning the chambers of the heart in the CT image slice with the chambers of the model of the heart, in accordance with an alternative exemplary embodiment of the present technique; and FIG. 9 is a schematic representation of still another technique for locally aligning the chambers of the heart in the CT image slice with the chambers of the model of the heart, in accordance with an alternative exemplary embodiment of the present technique.

DETAILED DESCRIPTION

Figure 1:
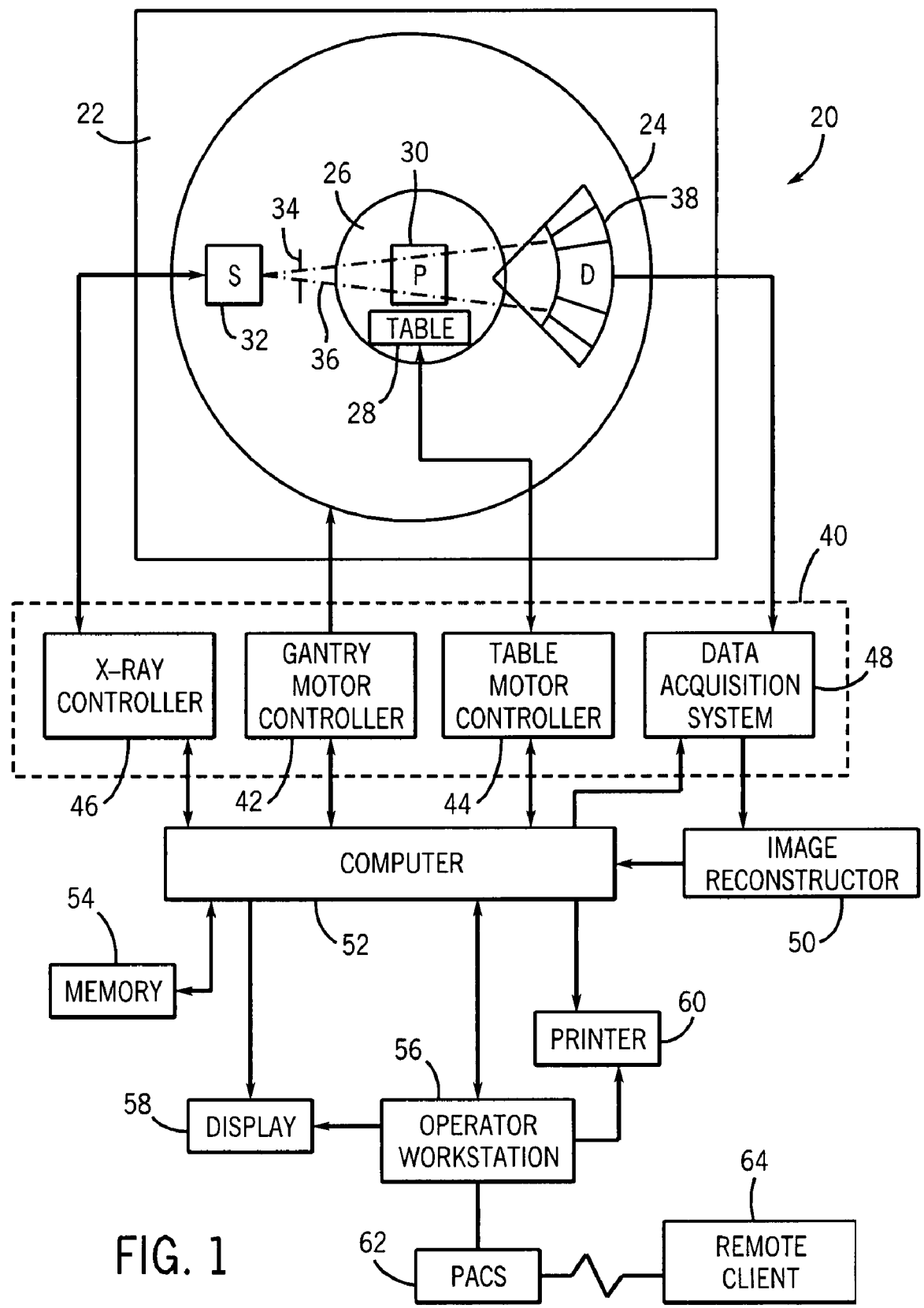
FIG. 1 is a schematic drawing of an imaging system, in accordance with an exemplary embodiment of the present technique.

Referring now to FIG. 1, a computed tomography (CT) imaging system designed both to acquire original image data and to process the image data for display and analysis is presented, and referenced generally by reference numeral 20. The illustrated embodiment of the CT imaging system 20 has a frame 22, a gantry 24, and an aperture (imaging volume or CT bore volume) 26. A patient table 28 is positioned in the aperture 26 of the frame 22 and the gantry 24. The patient table 28 is adapted so that a patient 30 may recline comfortably during the examination process.

The illustrated embodiment of the CT imaging system 20 has an X-ray source 32 positioned adjacent to a collimator 34 that defines the size and shape of the X-ray beam 36 that emerges from the X-ray source 32. In typical operation, the X-ray source 32 projects a stream of radiation (an X-ray beam) 36 towards a detector array 38 mounted on the opposite side of the gantry 24. All or part of the X-ray beam 36 passes through a subject, such as a human patient 30, prior to impacting the detector array 38. It should be noted that all or part of the X-ray beam 36 may traverse a particular region of the patient 30, such as the liver, pancreas, heart, and so on, to allow a scan of the region to be acquired. The detector array 38 may be a single slice detector or a multi-slice detector and is generally formed by a plurality of detector elements. Each detector element produces an electrical signal that represents the intensity of the incident X-ray beam 36 at the detector element when the X-ray beam 36 strikes the detector array 38. These signals are acquired and processed to reconstruct an image of the features within the patient 30.

The gantry 24 may be rotated around the patient 30 so that a plurality of radiographic views may be collected along an imaging trajectory described by the motion of the X-ray source 32 relative to the patient 30. In particular, as the X-ray source 32 and the detector array 38 rotate along with the CT gantry 24, the detector array 38 collects data of X-ray beam attenuation at the various view angles relative to the patient 30. Data collected from the detector array 38 then undergoes pre-processing and calibration to condition the data to represent the line integrals of the attenuation coefficients of the scanned patient 30. The processed data, commonly called projections, are then filtered and back projected to formulate an image of the scanned area. Thus, an image or slice is acquired which may incorporate, in certain modes, less or more than 360 degrees of projection data, to formulate an image.

Rotation of the gantry 24 and operation of the X-ray source 32 is controlled by a system controller 40, which furnishes both power and control signals for CT examination sequences. Moreover, the detector array 38 is coupled to the system controller 40, which commands acquisition of the signals generated in the detector array 38. The system controller 40 may also execute various signal processing and filtration functions, such as for initial adjustment of dynamic ranges, interleaving of digital image data, and so forth. In general, system controller 40 commands operation of the imaging system 20 to execute examination protocols and to process acquired data. In the present context, system controller 40 also includes signal processing circuitry, typically based upon a general purpose or application-specific digital computer, associated memory circuitry for storing programs and routines executed by the computer, as well as configuration parameters and image data, interface circuits, and so forth. The system controller 40 includes a gantry motor controller 42 that controls the rotational speed and position of the gantry 24 and a table motor controller 44 that controls the linear displacement of the patient table 28 within the aperture 26. In this manner, the gantry motor controller 42 rotates the gantry 24, thereby rotating the X-ray source 32, collimator 34 and the detector array 38 one or multiple turns around the patient 30. Similarly, the table motor controller 44 displaces the patient table 28, and thus the patient 30, linearly within the aperture 26. Additionally, the X-ray source 32 may be controlled by an X-ray controller 46 disposed within the system controller 40. Particularly, the X-ray controller 46 may be configured to provide power and timing signals to the X-ray source 32.

In the illustrated embodiment, the system controller 40 also includes a data acquisition system 48. In this exemplary embodiment, the detector array 38 is coupled to the system controller 40, and more particularly to the data acquisition system 48. The data acquisition system 48 typically receives sampled analog signals from the detector array 38 and converts the data to digital signals for subsequent processing. An image reconstructor 50 coupled to the computer 52 may receive sampled and digitized data from the data acquisition system 48 and performs high-speed image reconstruction. Alternatively, reconstruction of the image may be done by the computer 52. Once reconstructed, the image produced by the imaging system 10 reveals internal features of the patient 30.

The data collected by the data acquisition system 48, or the reconstructed images, may be transmitted to the computer 52 and to a memory 54. It should be understood that any type of memory to store a large amount of data may be utilized by such an exemplary imaging system 10. Also the computer 52 may be configured to receive commands and scanning parameters from an operator via an operator workstation 56 typically equipped with a keyboard and other input devices. An operator may control the CT imaging system 20 via the operator workstation 56. Thus, the operator may observe the reconstructed image and other data relevant to the system from computer 52, initiate imaging, and so forth.

The CT imaging system 20 also has a display 58 that is coupled to the operator workstation 56 and the computer 52 and may be utilized by a user to observe the reconstructed image, as well as to provide an interface for control of the operation of the CT imaging system 20. In this embodiment, a printer 60 is present to enable a hard copy of a medical image to be printed. The operator workstation 56 may also be coupled to a picture archiving and communications system (PACS) 62. It should be noted that PACS 62 may be coupled to a remote system 64, such as radiology department information system (RIS), hospital information system (HIS) or to an internal or external network, so that others at different locations may gain access to the image and to the image data.

It should be further noted that the computer 52 and operator workstation 56 may be coupled to other output devices, such as a standard or special purpose computer monitor and associated processing circuitry. One or more operator workstations 56 may be further linked in the CT imaging system 20 for outputting system parameters, requesting examinations, viewing images, and so forth. In general, displays, printers, workstations, and similar devices supplied within the CT imaging system 20 may be local to the data acquisition components, or may be remote from these components, such as elsewhere within an institution or hospital, or in an entirely different location, linked to the imaging system CT via one or more configurable networks, such as the Internet, virtual private networks, and so forth.

Figure 2:
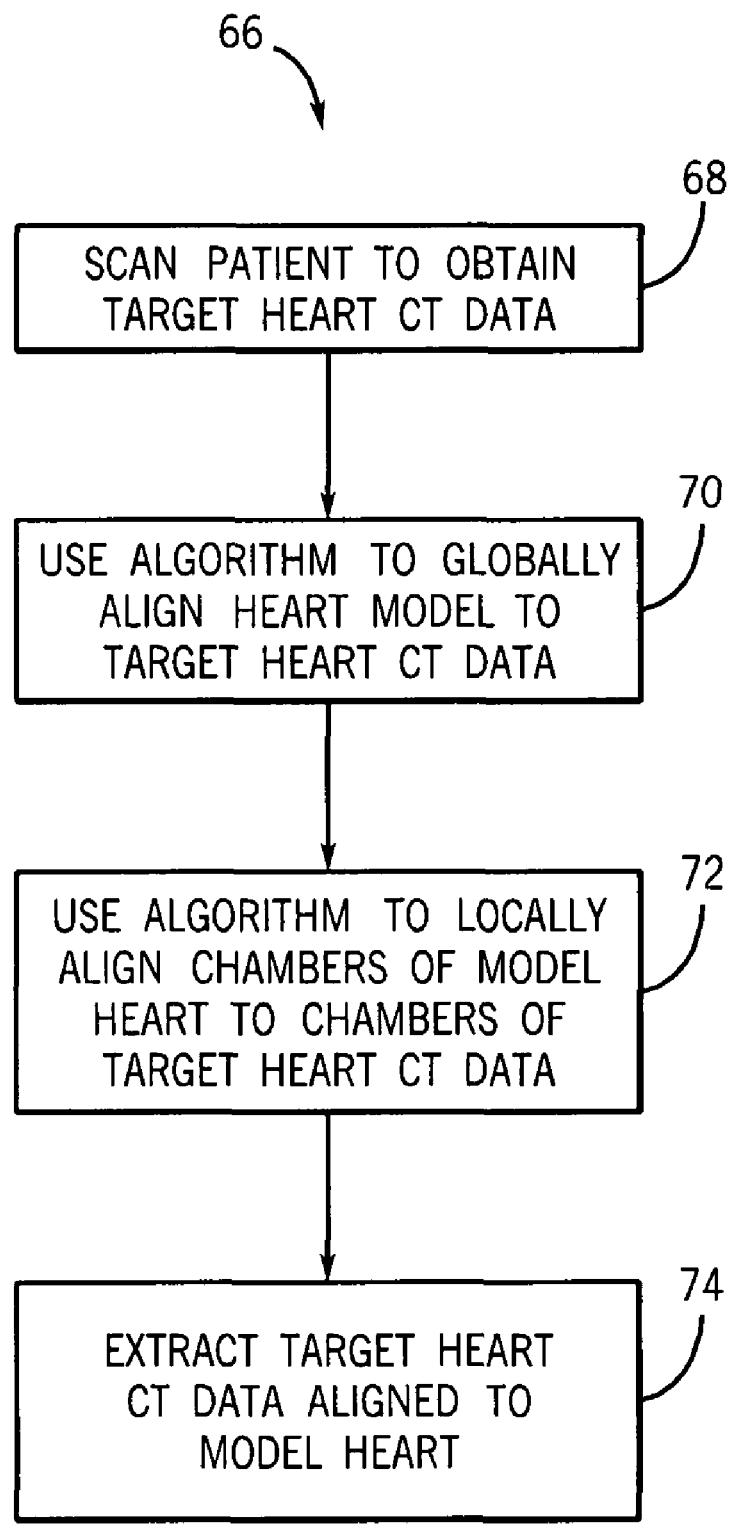
FIG. 2 is a block diagram of a technique for performing a segmentation of a medical image using a model of the organ to be segmented and a hierarchal alignment of the organ, in accordance with an exemplary embodiment of the present technique.

Referring generally to FIG. 2, a block diagram of a technique for segmenting and extracting a heart and its internal structures from CT image data using image data from a model of a heart is presented, and referenced generally by reference numeral 66. In the illustrated technique, a CT scan of the patient's thorax is taken to obtain heart CT image data, referenced generally by block 68. The heart CT image data is the target for the model of the heart during the alignment techniques described below. Also, please note that although a heart is utilized here, the technique is applicable to organs and anatomical features other than the heart. As will also be discussed in more detail below, a hierarchal approach is used to align the model of the heart with the heart CT image data. First, an algorithm is used to perform a global alignment of the model of the heart with the heart CT image data, referenced generally by block 70. Then, an algorithm is used to perform a local alignment of the individual chambers of the model of the heart with the individual chambers of the heart in the heart CT image data, referenced generally by block 72. However, internal structures of the heart other than the chambers may be used. Furthermore, other internal structures may be used when an organ other than the heart is to be aligned. In this embodiment, the portion of the heart CT image data that is aligned with the model of the heart is then extracted from the heart CT data that is not aligned with the model of the heart, represented generally by block 74.

In the illustrated embodiment, the CT scan of the patient's thorax, represented by block 68, is taken as part of a CT angiography utilizing a saline flush. During a CT angiography with a saline flush, a catheter is used to inject a contrast agent into the patient. The contrast agent, commonly called an X-ray dye, is mixed with the blood flowing within the artery. The contrast agent is injected into the patient's blood stream to make the blood flow visible for a short period of time, roughly 3-5 seconds, as the contrast agent is rapidly washed away into the coronary capillaries and then into the coronary veins. Without the contrast agent, the blood and the surrounding heart tissues would appear on a CT image only as a mildly-shape-changing, otherwise uniform, water density mass. As a result, the details of the blood and the internal heart structure would not be discernable.

The saline flush is added to the contrast agent in an attempt to recapture some of the contrast agent that is effectively lost in the venous system. In particular, the saline flush prevents contrast agent from collecting in the superior vena cava leading to the right atrium. However, this also leads to a washing out of the right atrium and right ventricle in CT images. As a result, segmentation algorithms that rely on intensity differences are complicated by the saline flush, and may be rendered ineffective. However, the present technique does not rely on intensity differences. Therefore, the present technique may receive the benefit of using a saline flush without the complications.

A number of different techniques may be used for developing the model of a heart used in the global alignment. A bank of CT image data containing segmented heart and chamber CT images may be used to develop the model of the heart. For example, one technique that may be used for developing the model of the heart may be described as a "best-case" model. The best-case model is an attempt to find the model that best represents the average shape of the population in the bank of CT image data. This "best-case" CT image, presumably, will undergo the least amount of deformation when matching the model of the heart to an actual CT image of a heart. To identify the best-case model of the heart, all of the images in the bank of CT image data are co-registered with each other and the overlaps are calculated creating a matrix of the Dice Similarity Coefficient (DSC) values. The image that is most central in the cluster i.e. having the highest coefficient of variance (COV) for DSC values is picked as the best-case model.

Another technique that may be utilized for developing a model of the heart may be described as the "average" model. Here, all of the segmented heart volumes from a bank of CT image data are aligned together and averaged, forming the averaged model. In iterative averaging, a random case from the database is chosen as the seed, to which all the other cases are registered. The intensities are then averaged; the average now becomes the seed to which all the heart volumes are registered in the subsequent iteration. This process is repeated until convergence occurs.

Yet another technique that may be utilized for developing a model of the heart may be described as a "population-based" model. The idea behind this technique is to pick the model from the CT image data that is closest to the target data in terms of a demographic profile. Data such as the gender, age, and the ethnicity of the patient are provided and stored within the bank of CT image data and may be utilized in developing the model of the heart. The implementation of this technique involves obtaining the gender information of the target case and matching it with the corresponding model.

In addition, various anatomical features in the model of the heart may be labeled as a result of the manual segmentation. The labeling information stored in the model of the heart may be transferred to the heart CT image data during alignment. After segmentation, the labeling information may be used to identify anatomical features in the heart CT image data.

Figure 3:
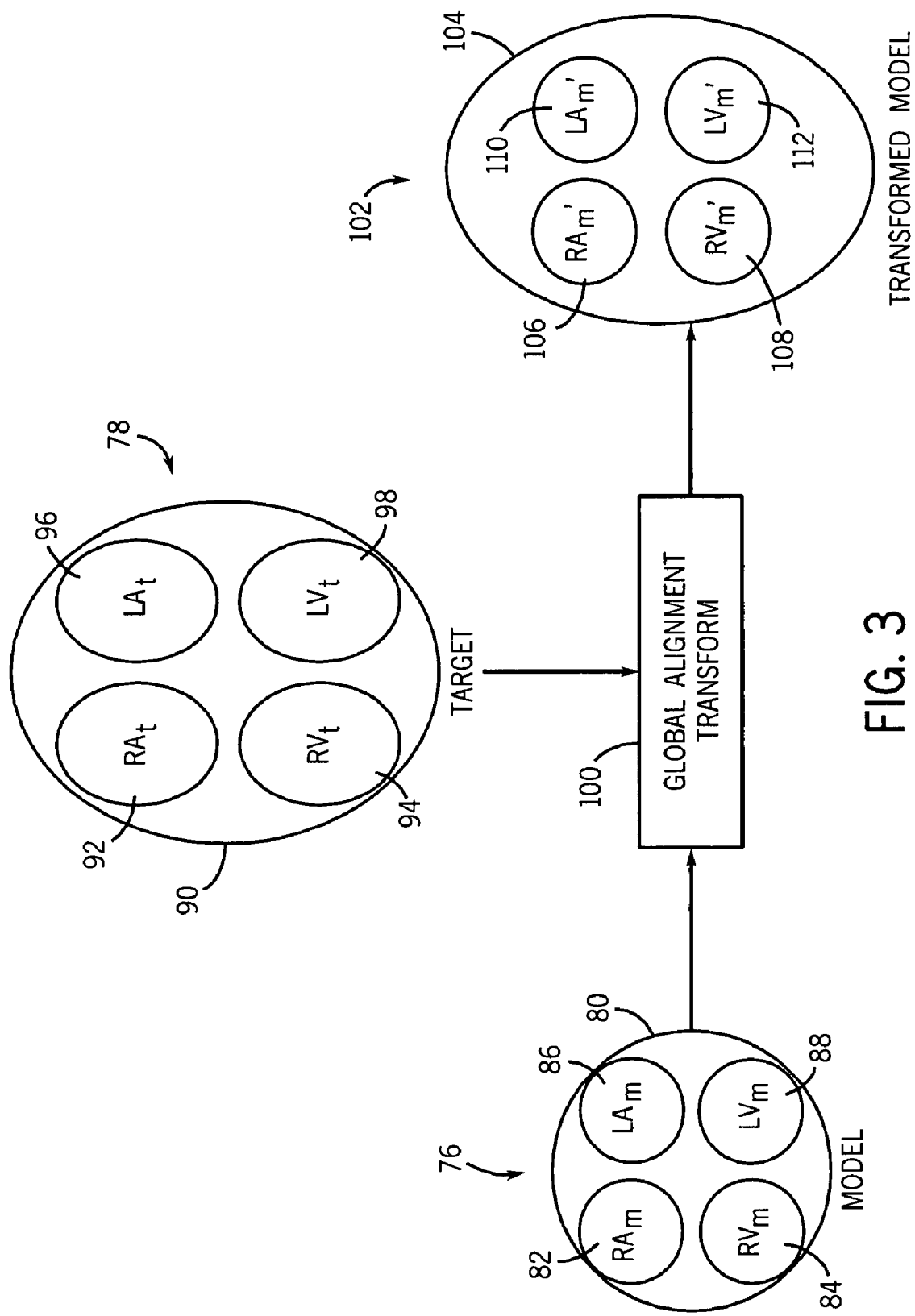
FIG. 3 is a schematic representation of a technique for globally aligning a heart to a model of the heart, in accordance with an exemplary embodiment of the present technique.

Referring generally to FIG. 3, a diagram representing the global alignment of a model of a heart 76 to a target heart 78 in the cardiac region of a heart CT image is provided. This global alignment corrects for differences in patient size, scan orientation, axial coverage mismatch, and gross anatomical variations between the model of the heart 76 and the target heart 78. The model of the heart 76 has an outer contour 80 that defines a volume, which is represented by a circle. Within the outer contour 80 of the model of the heart 76 are the four chambers of the model of the heart 76: a model right atrium 82, a model right ventricle 84, a model left atrium 86, and a model left ventricle 88, each represented by a circle. The target heart 78 has an outer contour 90 that defines the volume of the target heart 78. The outer contour 90 of the target heart 78 is represented by an oval. Within the outer contour 90 of the target heart 78 are the four chambers of the target heart: a target right atrium 92, a target right ventricle 94, a target left atrium 96, and a target left ventricle 98, each represented by an oval. The global alignment involves aligning the outer contour 80 of the model of the heart 76 to the outer contour 90 of the target heart 78.

A registration algorithm 100 is used to globally align the model of the heart 76 to the target heart 78. As a result a model of the heart globally aligned with the target heart 78 is established, represented generally by reference numeral 102. In this embodiment, the registration algorithm that is used is the mutual information metric. Mutual information (MI) is an information theoretic criterion that attempts to maximize the joint entropy between the two image sets. MI works independent of the spatial and intensity correspondence between the two image sets. However, other registration frameworks may be used. The globally-aligned model of the heart 102 has an outer contour 104 that defines the volume of the globally-aligned model of the heart 102, which is represented by an oval. The oval shape is used to reflect that the outer contour 104 of the model of the globally-aligned model of the heart 102 has been deformed to match the outer contour 80 of the target heart 78. Within this outer contour 104 are the four chambers of the model of the heart: a right atrium 106 of the globally-aligned model of the heart 102, a right ventricle 108 of the globally-aligned model of the heart 102, a left atrium 110 of the globally-aligned model of the heart 102, and a left ventricle 112 of the globally-aligned model of the heart 102, each represented by an oval.

The global alignment is used to correct for gross alignment errors between the model of the heart and the heart CT image data. While the model of the heart is selected based on "population" parameters or on a "best-suited" basis, the target heart of the heart CT image data is a volume taken from a different patient acquired under different scan conditions. Differences in axial coverage could create an offset between the heart location along this axis as well as difference in the anatomical information content in the two scans. For example, a "tight" cardiac scan with a small axial coverage (11 cms-15 cms) minimizes the inclusion of neighboring organs such as the liver, whereas, a multiple application scan (>20 cms) such as a triple rule out scan will include portions of the liver and ascending and descending aorta. Secondly, the differences in the display or reconstructed field of view could also affect the alignment of the model of the heart with the cardiac region of the heart CT image data. Typically, cardiac scans are reconstructed at 25 cms field of view ("FOV") but can vary from 18 cms to 40 cms depending on the size of the patient and the application. Variations in the size of the FOV affect the resolution as well as the anatomical information content. Moreover, the center of the FOV is chosen based on the application as well as the operator marking off the center of the anatomical region of interest. Therefore, large offsets in the heart location arising from anatomical variation, axial coverage, and the FOV require large translation corrections to align the heart. Scaling and rotation transforms can correct for variations in the size of the heart region and the tilt of the heart about the axial scan plane, respectively. At the end of the global alignment, the model of the heart is locked into the target heart region.

Figure 4:
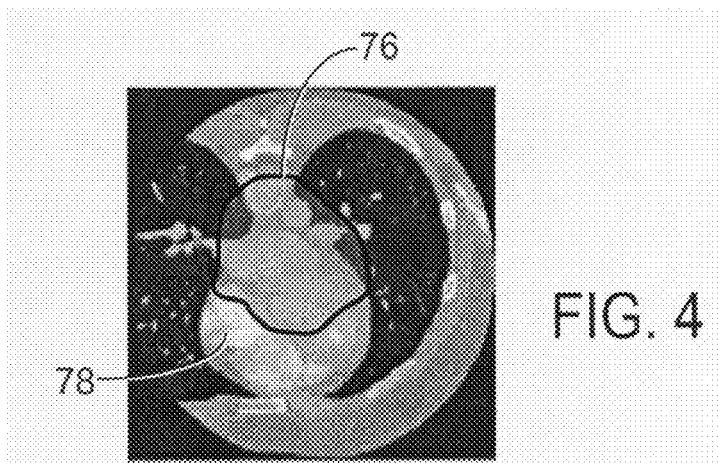
FIG. 4 is an example of an image slice from a CT imaging system and a model of the heart prior to global alignment, in accordance with an exemplary embodiment of the present technique.
Figure 5:
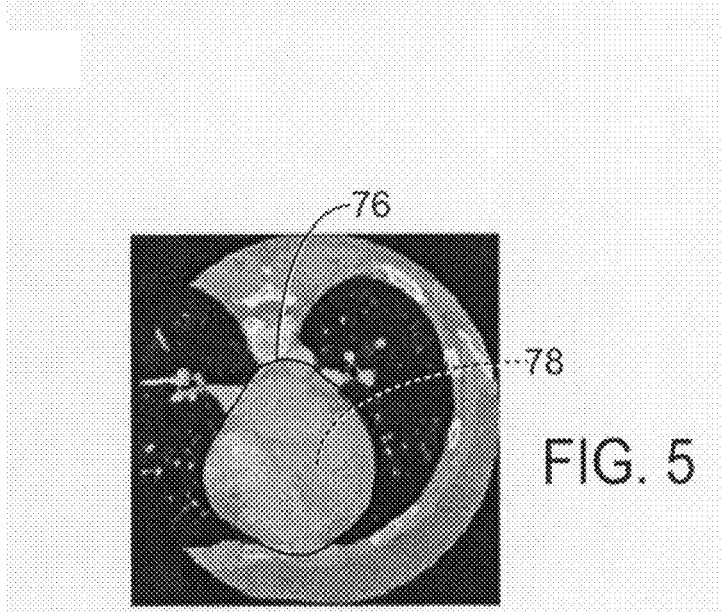
FIG. 5 is an example of an image slice from a CT imaging system and a model of the heart after global alignment, in accordance with an exemplary embodiment of the present technique.

Referring generally to FIGS. 4 and 5, examples of a model of the heart and a target heart in the cardiac region of a CT image prior to and after global alignment are provided. The outline of the model of the heart 76 has been emboldened for clarity. In FIG. 4, the model of the heart 76 is overlaid onto the target heart 78. In FIG. 5, the model of the heart 76 is globally aligned with the cardiac region of the heart CT image, which corresponds to the target heart 78. In this example, the model of the heart 76 has been rotated one hundred and eighty degrees and scaled to the size of the cardiac region of the heart CT image by the global alignment algorithm in order to align it with the target heart 78.

Figure 6:
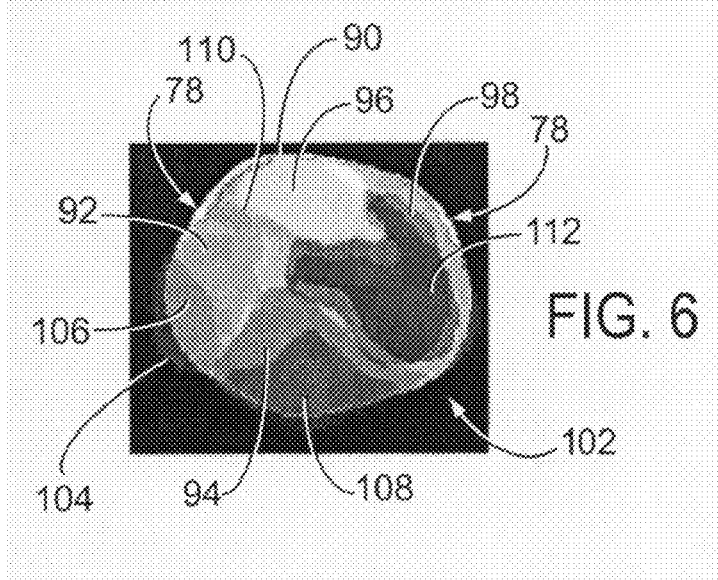
FIG. 6 is an example of the misalignment of the chambers of the heart in the CT image slice and the chambers of the model of the heart after global alignment, in accordance with an exemplary embodiment of the present technique.

Referring generally to FIG. 6, although the global alignment locks the heart boundary between the model of the heart and the target CT, it does not guarantee alignment of the internal structures of the heart, such as the chambers. The local alignment aligns the chambers of the model of the heart 76 to the target heart 78. Chamber alignment has an increased complexity because multiple structures need to be aligned, while maintaining anatomical integrity. Each internal structure, such as the left ventricle or right atrium, has a different size and shape and they vary quite widely from one subject to another. An example of the internal mismatch of the four chambers of the heart after global alignment is provided. As can be seen here, there is a general alignment between the outer contour 104 of the model of the globally-aligned model of the heart 102 and the outer contour 90 of the target heart 78. However, there exists a degree of misalignment between the chambers 106, 108, 110, 112 of the model of the globally-aligned model of the heart 102 and the chambers 92, 94, 96, 98 of the target heart 78. In accordance with the present technique, a second alignment, in this case a deformable alignment is performed to reduce the mismatch between the chambers in the globally-aligned model of the heart 102 and the chambers in the target heart 78.

Figure 7:
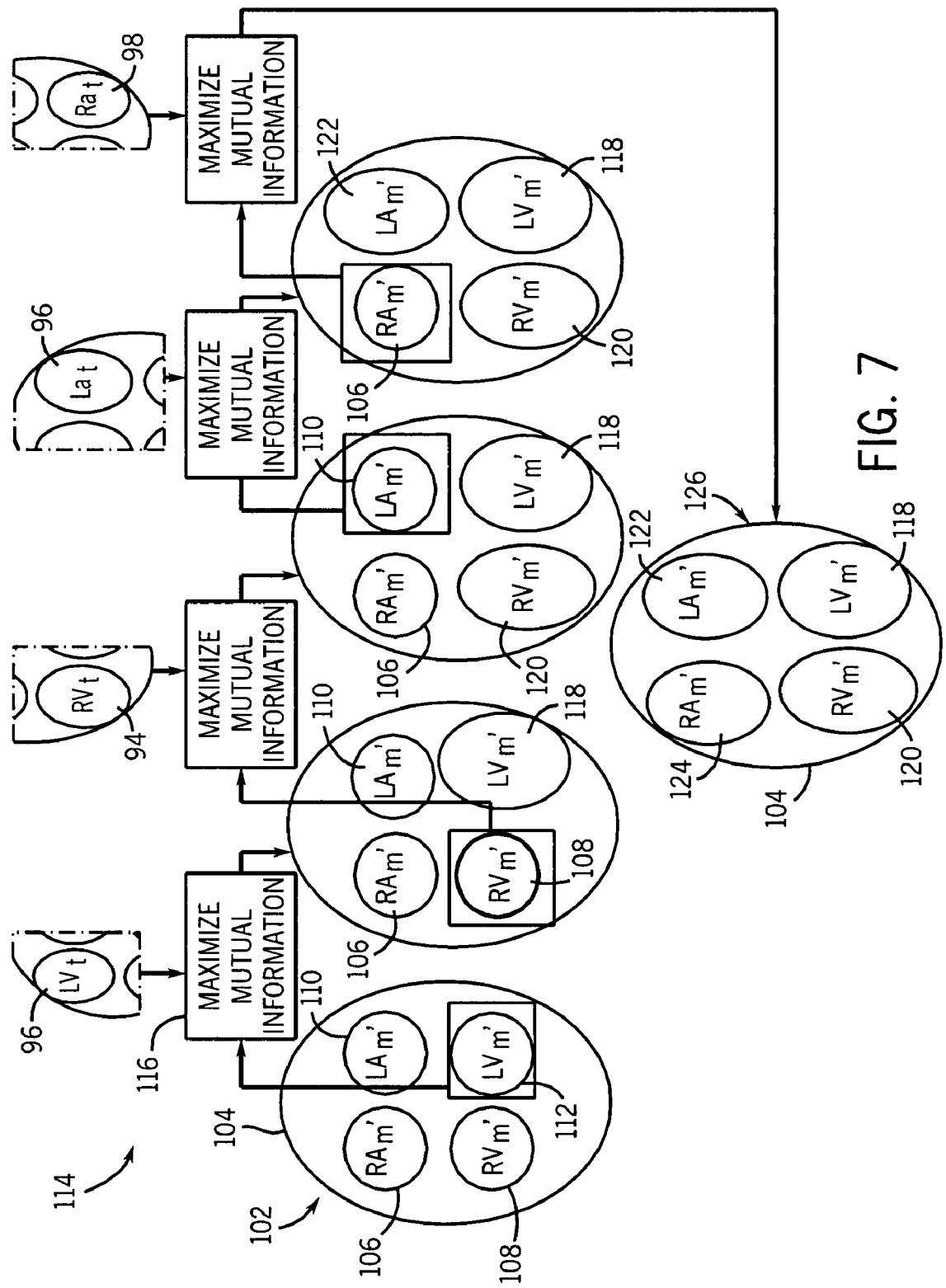
FIG. 7 is a schematic representation of a technique for locally aligning the chambers of the heart in the CT image slice with the chambers of the model of the heart, in accordance with an exemplary embodiment of the present technique.

Referring generally to FIG. 7, a technique for locally aligning each of the chambers of the globally-aligned model of the heart 102 with the chambers of the target heart 78 is presented, referenced generally by reference numeral 114. In this embodiment, an algorithm is used to align each chamber of the globally-aligned model of the heart 102 with its corresponding chamber in the target heart 78 in a sequential order. The process of locally aligning each of the chambers differs from the global alignment in that each chamber of the model of the heart is deformed to correspond to its corresponding chamber in the target heart, rather than the outer contour of the model heart as a whole. In this embodiment, the deformable alignment is performed sequentially for each of the four chambers. The alignment also provides the flexibility of choosing completely different registration transforms, metrics, optimizer scales, and search spaces for each of the chambers.

In the illustrated embodiment, the first chamber alignment performed is between the left ventricle 112 of the globally-aligned model of the heart 102 and the left ventricle 98 of the target heart 78. A mutual information algorithm 116 is used in this embodiment to perform the deformable alignment of each chamber. However, as noted above, different techniques for alignment may be used for each chamber of the heart. The resultant locally-aligned model left ventricle is represented generally by reference numeral 118. The next chamber for deformable alignment in this embodiment is the right ventricle 108 of the globally-aligned model of the heart 102. The locally-aligned model right ventricle is represented generally by reference numeral 120. Similarly, a locally-aligned model left atrium 122 and a locally-aligned model right atrium 124 are produced. The resultant globally-and-locally aligned heart model is represented by reference numeral 126.

Referring generally to FIG. 8, an embodiment of a technique for a deformable alignment of all of the chambers of the globally-aligned model of the heart 76 with the target heart 78 simultaneously is provided, and referenced generally by reference numeral 128. Transforms 130 are used to deform each chamber of the globally-aligned model of the heart 102 to align them with their corresponding chamber of the target heart 78. The algorithm produces a globally-and-locally aligned heart model 132 having a locally aligned left ventricle 134, a locally aligned right ventricle 136, a locally aligned left atrium 138, and a locally aligned right atrium 140.

In this embodiment, separate transforms 130 are computed for each chamber without a consistency check for maintaining anatomical integrity. The algorithm provides a region of interest or mask input region that restricts the reach of each chamber and minimizes the possibility of chamber overlap, but cannot prevent it. Thus, it is possible for there to be overlap between the chambers of the heart model, such as between the locally aligned left atrium 138 and the locally aligned right atrium 140 shown in FIG. 8. The outer contour 142 of the globally-and-locally aligned heart model 132 may be brought into local alignment by the effect of the various chamber alignments, as well.

Referring generally to FIG. 9, an alternative embodiment of a technique for deformable alignment of the chambers of the globally-aligned model of the heart 102 with the target heart in a simultaneously manner is provided, referenced generally by reference numeral 144. Transforms 146 are used to deform each chamber of the globally-aligned model of the heart 102 to align them with their corresponding chamber of the target heart 78. This algorithm has additional constraints to prevent chamber overlap and myocardium cross over. The alignment of the chambers might be sub-optimal but the anatomical integrity of the overall heart and chambers is maintained. The algorithm produces a globally-and-locally aligned heart model 148 having a locally-aligned left ventricle 150, a locally-aligned right ventricle 152, a locally-aligned left atrium 154, and a locally-aligned right atrium 156. The outer contour 158 of the globally-and-locally aligned heart model 148 may be brought into local alignment by the effect of the various chamber alignments, as well.

Upon completion of the alignment of the chambers of the heart in the model with the chambers of the heart in the CT image, the heart may be segmented from other anatomical features in the CT image. Those portions of the CT image that are aligned with the model are segmented, while those that are not may be removed. An image of the heart segmented from the other anatomical features in the thorax may then be produced. As the segmentation of the heart occurred without the need for comparisons of the intensities of voxels in the CT image, this technique for image segmentation is ideal for use with the saline flush protocol during CT angiography.

While only certain features of the invention have been illustrated and described herein, many modifications and changes will occur to those skilled in the art. It is, therefore, to be understood that the appended claims are intended to cover all such modifications and changes as fall within the true spirit of the invention.

The invention claimed is:

1. A computer-implemented method of segmenting image data, comprising:
   accessing patient image data representative of a portion of a patient's internal anatomy containing an anatomical feature;
   accessing image data representative of a model of the anatomical feature, wherein the model of the anatomical feature comprises a plurality of internal structural features;
   aligning the model of the anatomical feature with a region of the patient image data corresponding to the anatomical feature;
   aligning each of the plurality of internal structural features with their corresponding internal structural feature in the patient image data; and
   segmenting patient image data aligned with the model of the anatomical feature from patient image data not aligned with the model of the anatomical feature.

2. The computer-implemented method as recited in claim 1, wherein the anatomical feature is a heart and the plurality of internal structural features comprises a plurality of chambers of the heart.

3. The computer-implemented method as recited in claim 2, wherein accessing patient image data representative of a portion of a patient's internal anatomy containing an anatomical feature comprises performing a computed tomography angiography with a saline flush.

4. The computer-implemented method as recited in claim 2, wherein aligning each of the plurality of internal structural features with their corresponding internal structural feature in the patient image data, comprises deforming each of the plurality of chambers of the heart within the model of the anatomical feature to bring them into alignment with a corresponding chamber in the patient image data.

5. The computer-implemented method as recited in claim 1, wherein aligning each of the plurality of internal structural features with their corresponding internal structural feature in the patient image data, comprises aligning each of the plurality of internal structural features with its corresponding internal structural feature in the region of the patient image data in a sequential order.

6. The computer-implemented method as recited in claim 1, wherein aligning each of the plurality of internal structural features with their corresponding internal structural feature in the patient image data comprises aligning the plurality of internal structural features into alignment with their corresponding internal structural features simultaneously.

7. The computer-implemented method as recited in claim 1, wherein the image data representative of a model of an anatomical feature comprises at least one segmented medical image of the anatomical feature processed to establish the image data representative of a model of an anatomical feature.

8. The computer-implemented method as recited in claim 7, wherein the at least one segmented medical image of the anatomical feature is based on a demographic characteristic of the patient.

9. The computer-implemented method as recited in claim 8, wherein the demographic characteristic of the patient is gender.

10. The computer-implemented method as recited in claim 1, wherein the image data representative of a model of an anatomical feature is established from a single segmented medical image of the anatomical feature that best represents an average shape of a plurality of segmented medical images of the anatomical feature.

11. The computer-implemented method as recited in claim 1, wherein the image data representative of a model of an anatomical feature is established by averaging a plurality of segmented medical images of the anatomical feature.

12. The computer-implemented method as recited in claim 1, wherein aligning the model of the anatomical feature with a region of the patient image data corresponding to the anatomical feature comprises resizing the model of the anatomical feature to conform generally with the region of the patient image data corresponding to the anatomical feature.

13. The computer-implemented method as recited in claim 1, wherein the model of the anatomical feature comprises anatomical labeling data, the method comprising transferring the anatomical labeling data from the model of the anatomical feature to the patient image data.

14. A non-transitory machine-readable medium for processing medical image data, comprising:
   code operable for accessing patient image data representative of a portion of a patient's internal anatomy containing an anatomical feature;
   code operable for accessing image data representative of a model of the anatomical feature, wherein the model of the anatomical feature comprises a plurality of internal structural features;
   code operable for aligning the model of the anatomical feature with a region of the patient image data corresponding to the anatomical feature;
   code operable for aligning each of the plurality of internal structural features with their corresponding internal structural feature in the patient image data; and code operable for segmenting patient image data aligned with the model of the anatomical feature from patient image data not aligned with the model of the anatomical feature.

15. A system for processing medical image data, comprising:

means for accessing patient image data representative of a portion of a patient's internal anatomy containing an anatomical feature;

means for accessing image data representative of a model of the anatomical feature, wherein the model of the anatomical feature comprises a plurality of internal structural features;

means for aligning the model of the anatomical feature with a region of the patient image data corresponding to the anatomical feature;

means for aligning each of the plurality of internal structural features with their corresponding internal structural feature in the patient image data; and, means for segmenting patient image data aligned with the model of the anatomical feature from patient image data not aligned with the model of the anatomical feature.

* * * * *